United States Patent [19]

Ensslin

[11] Patent Number: 4,712,544
[45] Date of Patent: Dec. 15, 1987

[54] ELECTROSURGICAL GENERATOR

[75] Inventor: Frieder H. Ensslin, Rochester, N.Y.

[73] Assignee: Castle Company, Rochester, N.Y.

[21] Appl. No.: 828,472

[22] Filed: Feb. 12, 1986

[51] Int. Cl.⁴ .................................................. A61B 17/39
[52] U.S. Cl. ............................. 128/303.14; 128/303.17
[58] Field of Search .................. 128/303.13, 303.14, 128/303.17

[56] References Cited

U.S. PATENT DOCUMENTS

| | | | |
|---|---|---|---|
| 2,771,554 | 11/1956 | Gratzl | 128/421 |
| 3,964,487 | 6/1976 | Judson | 128/303.14 |
| 4,126,137 | 11/1978 | Archibald | 128/303.17 |
| 4,171,700 | 10/1979 | Farin | 128/303.17 |
| 4,188,927 | 2/1980 | Harris | 128/303.17 |
| 4,237,891 | 12/1980 | Du Bose et al. | 128/303.14 |

FOREIGN PATENT DOCUMENTS

| | | | |
|---|---|---|---|
| 0136855 | 4/1985 | European Pat. Off. | 128/303.13 |
| 58-94845 | 6/1983 | Japan | 128/303.13 |
| 2154881 | 9/1985 | United Kingdom | 128/303.14 |

*Primary Examiner*—Lee S. Cohen
*Attorney, Agent, or Firm*—Marjama & Pincelli

[57] ABSTRACT

An electrosurgical generator for use with a living being. The electrosurgical generator is provided with a circuit for determining real power output being delivered to a handpiece. A switching mechanism is also provided to allow alternate selection of the desired power to the desired output port.

7 Claims, 3 Drawing Figures

ELECTROSURGICAL GENERATOR

The present invention relates to an improved electrosurgical generator.

A typical electrosurgical generator of the prior art is provided with at least two operational modes, for example, a cutting mode and a coagulation mode. For each mode a power level setting is available to permit adjustment so as to obtain the desired amount of power at the working handpiece. The power level setting for each power mode is displayed by or in direct response to the rotational position of a potentiometer which controls the power level. In a typical electrosurgical generator the actual power level being delivered to the handpiece will quite often fluctuate during surgery. This fluctuation can be a result of temperature drift or partial generator failure and can present a very serious situation in that the operator of the device may be thinking that a pre-selected power level is being supplied to the handpiece when in fact a much higher or lower power level is being supplied.

Electrosurgical generators of the prior art which have more than one operational mode generally have more than one output port. Switch means are normally provided such that each operational mode is capable of being alternately selectively connected to the desired output port. In such units there is always the possibility that one, both or the wrong operational mode will be connected to the wrong or both output ports due to component failure.

An electrosurgical generator of the present invention is provided with means for determining and displaying real power output that is being delivered to the handpiece and means for connecting the desired power generating means to the desired output ports.

SUMMARY OF THE PRESENT INVENTION

In one aspect of the present invention an electrosurgical generator is provided with means for determining the true power output thereof which comprises an electrical circuit placed in line with the output of the electrical generating means. The circuit sends a signal back to the microproceser control for displaying the real power measurement being delivered to the handpiece.

In another aspect of the present invention, an electrosurgical generator is provided with at least two operational modes each of which is capable of being alternately selectively connected to one of at least two output ports. The switch mean comprises a movable member for placement in one of at least two positions such that when the movable member is in one of said positions electrical continuity is provided between the electrical operational modes and the desired output ports and when the movable member is in the second position the electrical operational modes to the output ports is reversed.

DETAILED DESCRIPTION OF THE PREFERRED EMBODIMENT

Figure 1:
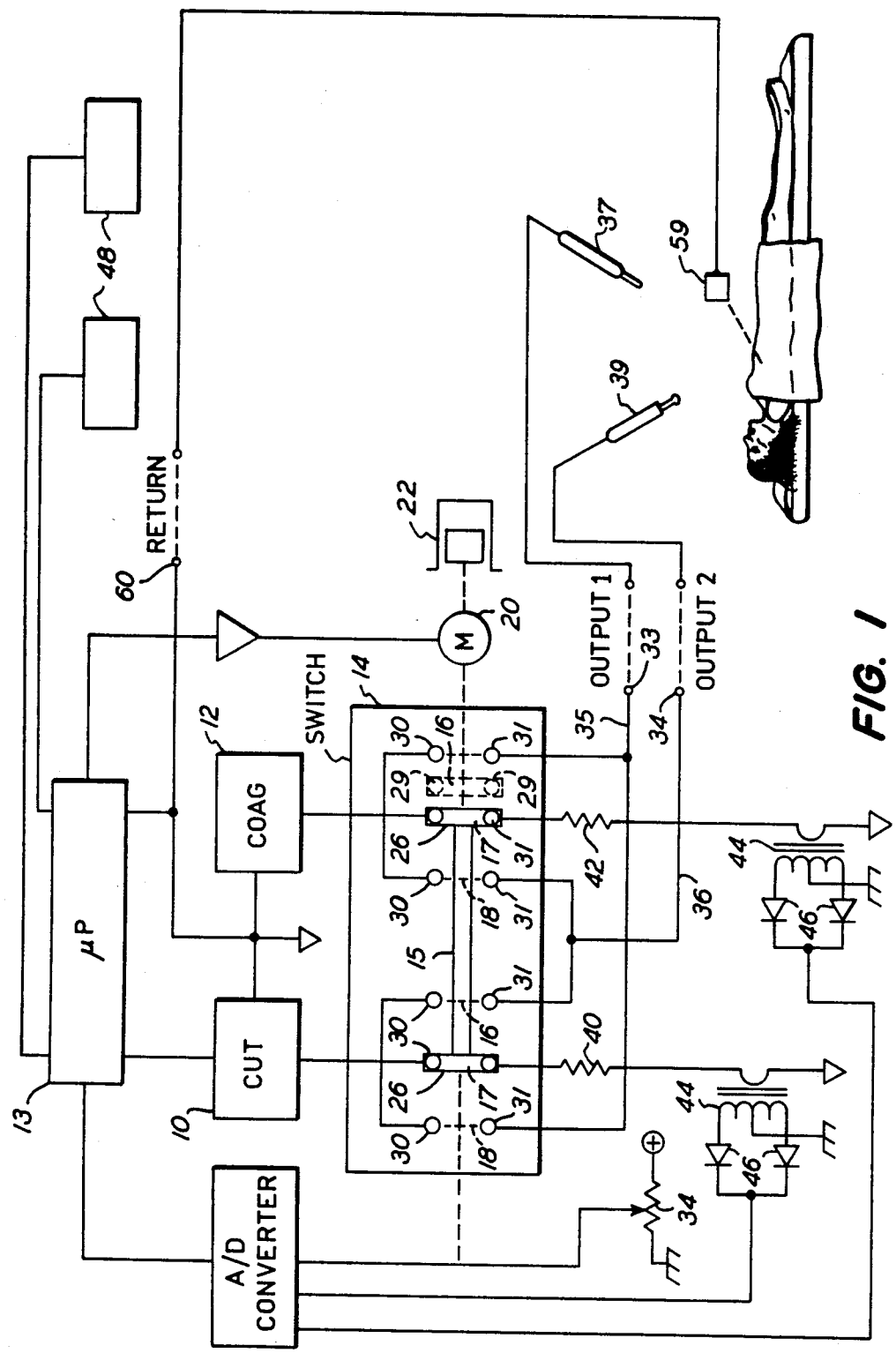
FIG. 1 is a combined schematic and blocked diagram illustrating the circuitry for determining real power output of electrosurgical generator as applied to the output port.

In the drawings, like references refer to like elements.

Referring to FIG. 1 it is shown a combined schematic and blocked diagram of illustrated circuitry for providing real power output measurement of electrosurgical generator to a display and for allowing only one electrosurgical power generator means or operational mode to be electrically connected at any given time to a common output port.

A first electrical power generating means 10 is provided for generating a radio frequency output for cutting of living tissue and a second electrical power generating means 12 generates a second radio frequency output so as to permit coagulation of living tissue as is well known in the art. It is understood that any desired radio frequency may be used. A microprocessor 13 controls whether the first or second electrical power generating means 10, 12 will be in the active generating mode. The outputs of first and second electrical power generating means 10, 12 are each connected to switch 14. Switch 14 is provided with a movable integral member 15 which is capable of being placed in one of three axially spaced positions 16, 17, or 18 associated with each power generating means 10, 12. Accordingly, member 15 will be moved between positions 16, 17, and 18 for each power generating means at the same time. Preferably member 15 is a single unitary part. In the particular embodiment illustrated movable member 15 is placed in one of these positions by lineal motor 20 which is connected to member 15 by appropriate linkage (not shown). While the particular embodiment illustrated shows only three positions, any desired number of positions may be provided in switch 14. The use of a lineal motor 20 allows the positioning of member 15 at any point along its path. Motor 20 is driven in the desired direction by microprocessor 13. The microprocessor 13 receives information about the position of movable member 15 by potentiometer 34 which is connected to one end 26 of movable member 15 (by appropriate finger not shown) such that the potentiometer 34 will move in response to the position of member 15. When the microprocessor 13 senses that the switch is positioned a relatively great distance from its intended position or that the speed of movement of the switch toward its desired positions is slow the processor will generate a continuous DC signal of such polarity to the lineal motor 20 such that it will be driven toward the intended position with the greatest amount of energy available. When the microprocessor 13 senses that the intended position is nearly achieved or that the speed of movement is relatively great it will generate pulses of proportionally decreasing width the more the latter two conditions comes to exist. When the member 15 has arrived at its intended position the microprocesser 13 will cease to issue drive signal.

In the particular embodiment illustrated the lineal drive motor 20 is coupled with a damper 22 so that movement between positions can be done quickly and smoothly. In the particular embodiment illustrated damper 22 is a pneumatic cylinder. Damper 22 may be omitted if so desired.

Movable member 15 is provided with a pair of electrical contacts 29 at each longitudinal end 26 thereof for contact with contacts 30, 31. Each pair of electrical contacts 29 are electrically connected so as to provide electrical continuity across each end 26. A set of corresponding input and output contacts 30, 31 respectively, are provided at positions 16, 17, 18 for each power generating means 10, 12. It can be seen that the contacts 29 of movable member 15 will provide the appropriate electrical continuity between the inputs and outputs contacts 30, 31 depending on which position movable member 15 is positioned.

In the particular embodiment illustrated switch 14 is electrically connected to two output ports 33, 34 by common output circuits 35, 36 respectively. The output contacts of position 16 of first power generating means 10 and the output contact 31 of position 18 of second power generating means are electrically connected to common output port 34 by output circuit 36. In similar manner the output contact 31 of position 18 of first generating means and the output contact 31 of portion 16 of second power generating means are electrically connected to common output port 33 by common output unit 35. The output contacts 31 of position 17 of first and second power generating means are each connected to resistors 40, 42 respectively.

When the movable member 15 is in position 16 second power generating means 12 is electrically connected to common output 33 and first power generating means 10 is electrically connected to common output port 34. In operation of the electrosurgical unit only one power generating means will generally be activated by microprocessor 13 thereby allowing the desired operational mode to supplied to the desired output port. However, power may be supplied at one port or at both output ports 33, 34 at the same time. As illustrated, one port may provide a cutting mode while the other providing a coagulation mode.

By providing the switching arrangement of FIG. 1 there may be provided two handpieces 37, 39 which are connected to ports 33, 34 respectively. When member 15 is in position 16 the coagulation mode be provided to handpiece 37 and a cutting mode would be provided to handpiece 39. The present switching arrangement also minimizes or eliminates the possibility that the patient can be burned by the second handpiece not being used by the physician or operator. A return plate 59 connected to the patient is electrically connected to return port 60.

When the movable member 15 is in position 17 the output of either the first electrical power generating 10 or second electrical power generating means 12 (as the case may be) will be delivered to either resistor 40 or 42 which are each respectively connected to ground. A current tranformer is connected to the output of each of the first or second power generating means after resistor 40 or 42. Current transformers 44 are each electrically connected to an A/D (analog to digital) converter through rectifiers 46. The A/D converter reads the appropriate current value signal being delivered, which relates directly to the actual output of either the first or second power generating means 10, 12. This measurement is then relayed to the microprocessor 13 for display on display terminal 48. When the movable member 15 is in the measuring position 17 microprocessor 13 provides power only for a sufficient amount of time so that an appropriate measurement may be made. Generally, only a few milliseconds are required. It is important that real power measurement be taken when a known constant load is being applied to the power generating means. The switch 14 allows power to deliver to resistors 40, 42 of known quality. In the particular embodiment illustrated resistor 40 is 250 ohms and resistor 42 is 400 ohms and are preferably matched to the output of its associated power generating means. The movable member 15 will assume the measuring position 17 generally under one of two conditions, when the electrosurgical unit is initially powered up and secondly when the microprocessor 13 senses, that one of the potentiometers which controls power adjustment has been removed by more than approximately 1° angle. Movement of 1° refers to the amount in which the corresponding dials which controls the adjustment is moved in the rotational direction. It is, of course, understood the amount of change in power adjustment level that will cause a true power measurement, may be based on any desired value, for example, on incremental values of the power or voltage selector, or different values for the amount of movement of the power selector. Preferably a third condition is provided when the switch 14 will be placed in the measuring mode. This third condition is preferably selected to occur every time a radio frequency is shut down, that is, when the operator turns off either the foot or hand control device, even for a brief second. In this way a continuous update will be flashed to the appropriate display panel 40.

The preferred form of the present invention has been described as having three separate distinct positions for switch 14, however, various other modifications may be made with departing from the scope of the present invention.

Figure 2:
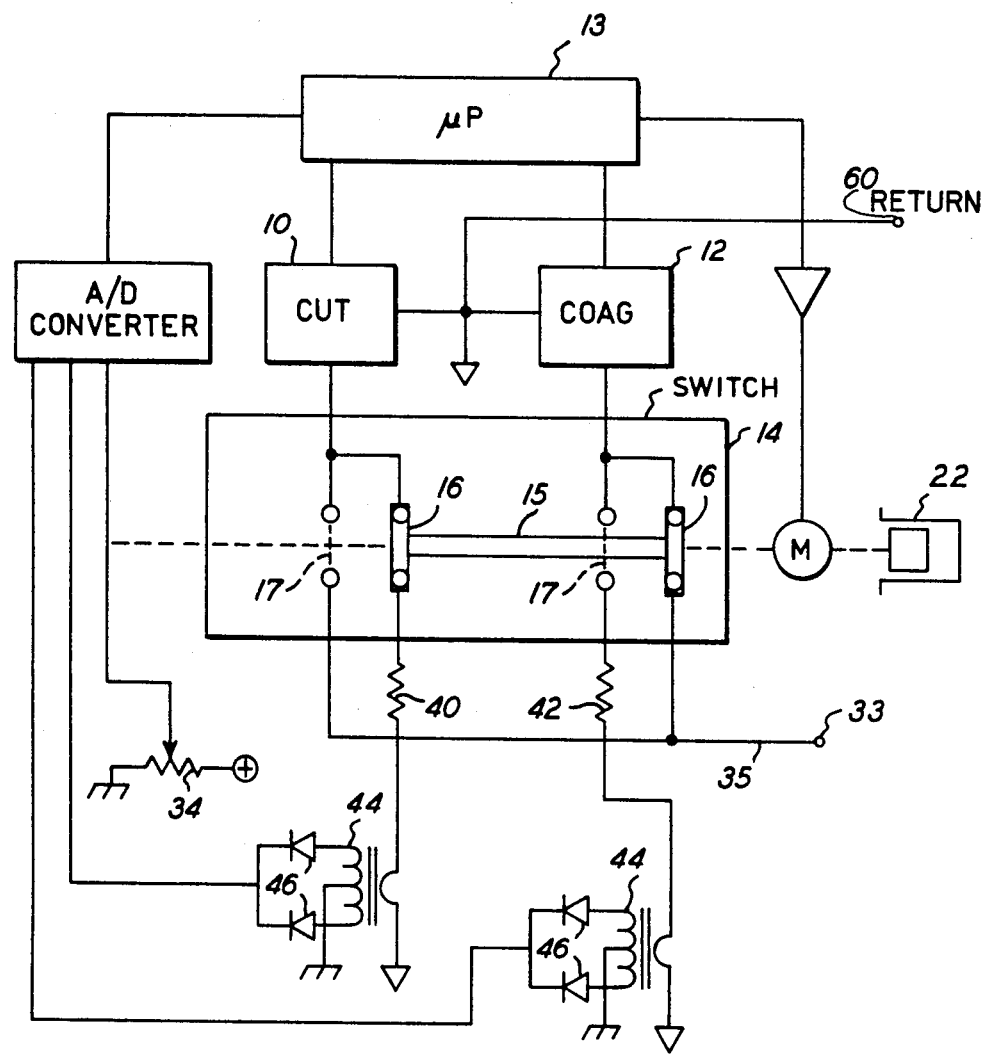
FIG. 2 is a combined schematic and blocked diagram illustrated circuitry of alternate embodiment of the present invention for providing real power output measurement and allowing only one electrical power generating means to be electrically connected to the output port at any given time.

Referring to FIG. 2 there is illustrated a modified form of the present invention wherein only two positions 16 and 17 are provided. In this embodiment only a single common output port 33 is provided. Movable member 15 in position 16 second power generating means 12 will be electrically connected to common output port 33 or real power measurement of first power generating means may be obtained. Whereas when movable member 15 is in position 17 will allow real power measurement of second power generating may be taken or first power generating means 10 may be electrically connected to common output 33. In this embodiment it is assured that only one power generating means will be connected to the common output.

Figure 3:
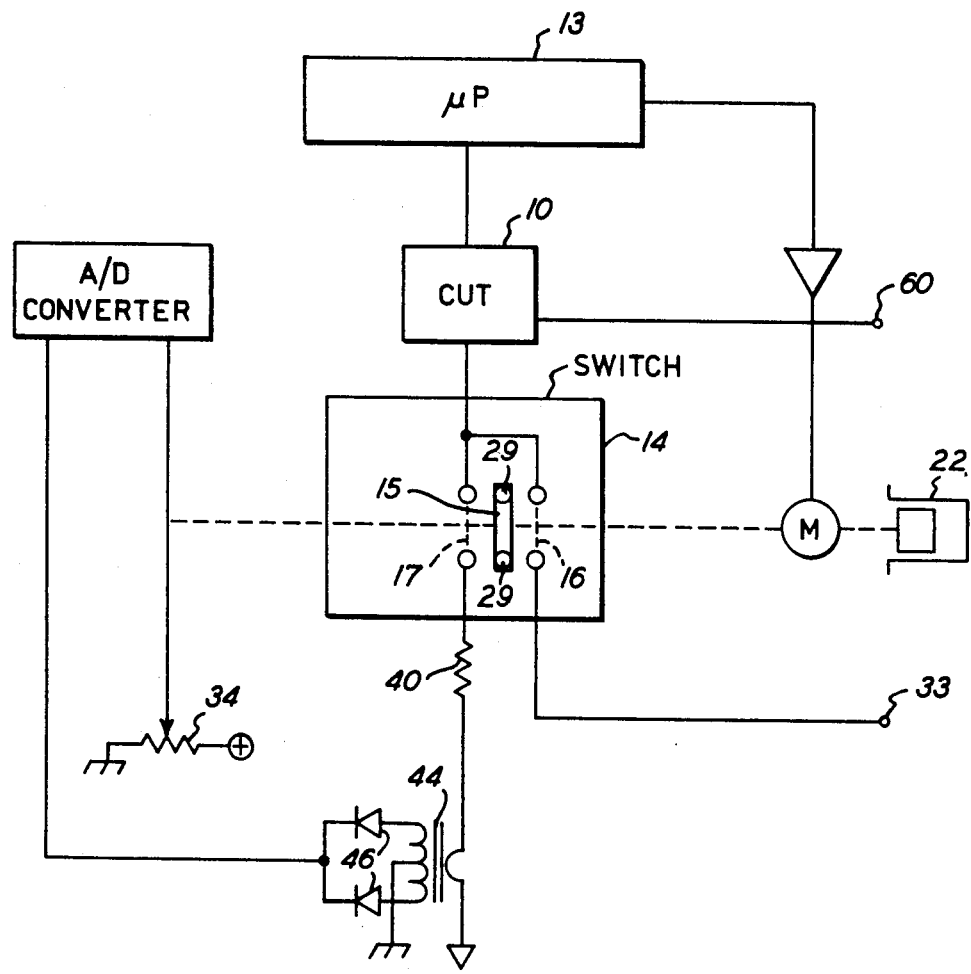
FIG. 3 is a combined schematic and blocked diagram illustrated circuitry for providing real power output measurements to a display wherein only a single electrical power generating means is provided.

Referring to FIG. 3, only one electrical power generating means 10 is provided. In the embodiment illustrated a cutting mode is provided, however, any other desired mode may be provided as desired. Movable member 15 when in position 16 will be connected to output port 33 and when in position 17 will allow real power measurement.

I claim:

1. An electrosurgical generator for use with a living being comprising:
   at least one electrical power generating means;
   a first output port;
   a first output circuit connected to said first output port for connecting the output of said at least one electrical power generating means to said first output port;
   a measuring circuit having a known constant load, said measuring circuit being isolated from said first output circuit;

switch means for selectively connecting the output of said at least one power generating means to said measuring circuit or said first output circuit;

means for determining real power output of said at least one power generating means when said at least one power generating means is connected to said measuring circuit, said measuring circuit comprising a transformer placed in series with said known constant load for measuring the output current of said at least one power generating means, a full wave rectifier connected to the output of the secondary side of said transformer, an A/D converter connected to said rectifier, a microprocessor connected to said A/D converter for receiving a signal from said A/D converter and for displaying true power output, said at least one electrical power generating means comprises two electrical power generating means, said electrosurgical generator comprising a second output port, a second output circuit connected to said second output port for connecting said first or second electrical power generating means to said second output port, said switch means being capable of allowing said first or second power generating means to be alternately selectively electrically connected to said first or second output circuit, said switch means having a first set and second set of corresponding input and output contacts associated with each of said power generating means so as to provide a first and second axially spaced switch positions associated with each of said first and second electrical power generating means, a movable switch member for moving between said first and second switch positions associated with each of said electrical power generating means at the same time, said movable member having means for providing electrical continuity between said one set of input and output contacts associated with each power generating means with said first or second output circuit.

2. An electrosurgical generator for use with a living being comprising:
first and second electrical power generating means;
a first output port;
a first output circuit connected to said first output port for connecting said first or second electrical power generating means to said first output port;
a second output port;
a second output circuit connected to said second output port for connecting said first or second electrical power generating means to said second output port;
a measuring circuit having a known constant load, said measuring circuit being isolated from said first or second output circuits;
switch means for selectively connecting the output of said first or second electrical power generating means to said measuring circuit, first output circuit or second output circuit;
means for determining true power output of said first or second electrical generating means when said first or second electrical generating means is connected to said measuring circuit;
said measuring circuit comprising a transformer placed in series with said known constant load for measuring the output current of said first or second power generating means, a full wave rectifier connected to the output of the secondary side of said transformer, an A/D converter connected to said rectifier, a microprocessor connected to said A/D converter for receiving a signal from said A/D converter and for displaying true power output and for activating said first and/or second power generating means, said switch means comprises a first set, second set and third set of corresponding input and output contacts associated with each of said power generating means so as to provide first, second and third axially spaced switch positions associated with each of said first and second electrical power generating means, a movable switch member for moving between said first, second and third switch positions associated with each of said electrical power generating means at the same time, said movable member having means for providing electrical continuity between said one set of said input and output contacts associated with each said power generating means with said first or second output circuit.

3. An electrosurgical generator for use with a living being comprising:
first and second electrical power generating means;
a first output port;
a second output port;
a first output circuit connected to said first output port for connecting said first or second electrical power generating means to said first output port;
a second output port circuit connected to said second output port for connecting said first or second electrical power generating means to said second output port;
a microprocessor having means for activating either said first or second power generating means;
switch means for alternately selectively connecting the output of said first or second electrical power generating means to said first output circuit or second output circuit; said switch means having a first set and second set of corresponding input and output contacts associated with each of said power generating means so as to provide first and second axially spaced switch positions associated with each of said first and second electrical power generating means, a movable switch member for moving between said first and second switch positions associated with each of said electrical power generating means at the same time, said movable member having means for providing electrical continuity between said one set of said input and output contacts associated with each said power generating means with said first or second output circuit.

4. An electrosurgical generator according to claim 3 wherein an electric motor is connected to said movable member in said switch means so as to control movement of said movable member.

5. An electrosurgical generator according to claim 4 wherein a damper is connected to said movable member so as to dampen the movement of said movable member between positions.

6. An electrosurgical generator according to claim 3 further comprising means for determining the position of said movable switch member.

7. An electrosurgical generator according to claim 6 wherein said means for determining the position of said movable switch member comprises a potentiometer which is connected to said movable member and produces a variable signal in response to the position of said member, said microprocessor having means for reading said signal.

* * * * *